United States Patent [19]

Phillips et al.

[11] Patent Number: 5,049,487
[45] Date of Patent: Sep. 17, 1991

[54] AUTOMATED INITIATION OF TIMING OF REFLECTANCE READINGS

[75] Inventors: Roger Phillips, Palo Alto; Geoffery McGarraugh, Scotts Valley; Frank Jurik, San Mateo; Ray Underwood, Red Bluff, all of Calif.

[73] Assignee: Lifescan, Inc., Milipitas, Calif.

[21] Appl. No.: 154,983

[22] Filed: Feb. 11, 1988

Related U.S. Application Data

[62] Division of Ser. No. 896,418, Aug. 13, 1986, Pat. No. 4,935,346.

[51] Int. Cl.$^5$ .......................... C12Q 1/00; G01N 21/77
[52] U.S. Cl. ........................................ 435/4; 435/805; 435/14; 436/46; 436/50; 436/162; 436/165; 436/169; 422/56; 422/57; 422/58; 422/67
[58] Field of Search ....... 435/7, 805, 14, 4, 7.92–7.95; 436/46, 50, 162, 165, 169; 422/58, 66, 56, 82.05, 57, 67; 128/630

[56] References Cited

U.S. PATENT DOCUMENTS

| | | | |
|---|---|---|---|
| 3,992,158 | 11/1976 | Przybylowicz et al. | 422/58 |
| 4,059,405 | 11/1977 | Sodickson et al. | 422/56 X |
| 4,420,566 | 12/1983 | Jessop et al. | 436/46 |
| 4,627,445 | 12/1986 | Garcia et al. | 128/770 |
| 4,637,403 | 1/1987 | Garcia et al. | 128/770 |
| 4,787,398 | 11/1988 | Garcia et al. | 128/770 |

OTHER PUBLICATIONS

Tietz (ed.), Textbook of Clinical Chemistry, (W. B. Saunders Company, Philadelphia) 1986, pp. 267–269.

Primary Examiner—Esther L. Kepplinger
Assistant Examiner—Carol A. Spiegel
Attorney, Agent, or Firm—Richard L. Neeley

[57] ABSTRACT

A method for determining the presence of an analyte in a fluid is described along with various components of an apparatus specifically designed to carry out the method. The method involves taking a reflectance reading from one surface of an inert porous matrix impregnated with a reagent that will interact with the analyte to produce a light-absorbing reaction product when the fluid being analyzed is applied to another surface and migrates through the matrix to the surface being read. Reflectance measurements are made at two separate wavelengths in order to eliminate interferences, and a timing circuit is triggered by an initial decrease in reflectance by the wetting of the surface whose reflectance is being measured by the fluid which passes through the inert matrix. The method and apparatus are particularly suitable for the measurement of glucose levels in blood without requiring separation of red blood cells from serum or plasma.

2 Claims, 3 Drawing Sheets

AUTOMATED INITIATION OF TIMING OF REFLECTANCE READINGS

This is a division of application Ser. No. 896,418, filed Aug. 13, 1986, now U.S. Pat. No. 4,935,346.

FIELD OF THE INVENTION

The present invention relates to a test device and method for the colorimetric determination of chemical and biochemical components (analytes) in aqueous fluids, particularly whole blood. In one preferred embodiment it concerns a test device and method for colorimetrically measuring the concentration of glucose in whole blood.

BACKGROUND OF THE INVENTION

The quantification of chemical and biochemical components in colored aqueous fluids, in particular colored biological fluids such as whole blood and urine and biological fluid derivatives such as serum and plasma, is of ever-increasing importance. Important applications exist in medical diagnosis and treatment and in the quantification of exposure to therapeutic drugs, intoxicants, hazardous chemicals and the like. In some instances, the amounts of materials being determined are either so miniscule—in the range of a microgram or less per deciliter—or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels the patient and physician together make adjustments in diet, exercise and insulin intake to better manage the disease. Clearly, this information should be available to the patient immediately.

Currently a method widely used in the United States employs a test article of the type described in U.S. Pat. No. 3,298,789 issued Jan. 17, 1967 to Mast. In this method a sample of fresh, whole blood (typically 20-40 μl) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another popular blood glucose test method employs similar chemistry but in place of the ethylcellulose-coated pad employs a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then in the first case the blood sample is washed off with a stream of water while in the second case it is wiped off the film. The reagent pad or film is then blotted dry and evaluated. The evaluation is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator colorimetric determinations in that their result is based on an absolute color reading which is in turn related to the absolute extent of reaction between the sample and the test reagents. The fact that the sample must be washed or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing can give low results and underwashing can give high results.

Another problem that often exists in simple lay-operator colorimetric determinations is the necessity for initiating a timing sequence when blood is applied to a reagent pad. A user will typically have conducted a finger stick to a obtain a blood sample and will then be required to simultaneously apply the blood from the finger to a reagent pad while initiating a timing circuit with his or her other hand, thereby requiring the use of both hands simultaneously. This is particularly difficult since it is often necessary to insure that the timing circuit is started only when blood is applied to the reagent pad. All of the prior art methods require additional manipulations or additional circuitry to achieve this result. Accordingly, simplification of this aspect of reflectance reading instruments is desirable.

The presence of red blood cells or other colored components often interferes with the measurements of these absolute values thereby calling for exclusion of red blood cells in these two prior methods as they are most widely practiced. In the device of U.S. Pat. No. 3,298,789 an ethyl cellulose membrane prevents red blood cells from entering the reagent pad. Similarly, the water-resistant film of U.S. Pat. No. 3,630,957 prevents red blood cells from entering. In both cases the rinse or wipe also acts to remove these potentially interfering red blood cells prior to measurement.

Accordingly, there remains a need for a system of detecting analytes in colored liquids, such as blood, that does not require removal of excess liquid from a reflectance strip from which a reflectance reading is being obtained.

SUMMARY OF THE INVENTION

Novel methods, compositions and apparatus are provided for diagnostic assays comprising a hydrophilic porous matrix containing a signal producing system and a reflectance measuring apparatus which is activated upon a change in reflectance of the matrix when fluid penetrates the matrix. The method comprises adding the sample, typically whole blood, to the matrix which filters out large particles, such as red blood cells, typically with the matrix present in the apparatus. The signal-producing system produces a product which further changes the reflectance of the matrix, which change can be related to the presence of an analyte in a sample.

Exemplary of the diagnostic assay system is the determination of glucose in the whole blood, where the determination is made without interference from the blood and without a complicated protocol subject to use error.

BRIEF DESCRIPTION OF THE DRAWINGS

The present invention can be more readily understood by reference to the following detailed description when read in conjunction with the attached drawings, wherein.

DETAILED DESCRIPTION OF THE INVENTION

THE REAGENT ELEMENT

Figure 1:
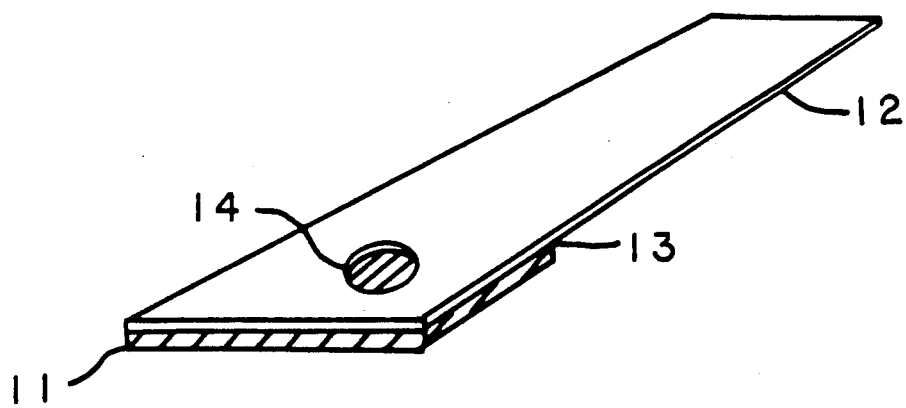
FIG. 1 is a perspective view of one embodiment of a test device containing the reaction pad to which the fluid being analyzed is applied.

The subject invention provides an improved rapid and simple methodology employing reliable and easy to operate apparatus for the determination of analytes such as glucose, particularly involving an enzyme substrate which results in the production of hydrogen peroxide as an enzyme product. The method involves applying to a porous matrix a small volume of whole blood, sufficient to saturate the matrix. Bound to the matrix are one or more reagents of a signal producing system, which results in the production of a product resulting an initial change in the amount of reflectance of the matrix. The matrix is typically present in a reflectance-measuring apparatus when blood is applied. The liquid sample penetrates the matrix, resulting in an initial change in reflectance at the measurement surface. A reading is then taken at one or more times after the initial change in reflectance to relate the further change in reflectance at the measurement surface or in the matrix as a result of formation of the reaction product to the amount of analyte in the sample.

For measurements in blood, particularly glucose measurements, whole blood is typically used as the assay medium. The matrix contains an oxidase enzyme which produces hydrogen peroxide. Also contained in the matrix will be a second enzyme, particularly a peroxidase, and a dye system which produces a light-absorbing product in conjunction with the peroxidase. The light-absorbing product changes the reflectance signal. With whole blood, readings are taken at two different wavelengths with the reading at one wavelength used to subtract out background interference caused by hematocrit, blood oxygenation, and other variables which may affect the result.

A reagent element is employed which comprises the matrix and the members of the signal producing system contained within the matrix. The reagent element may include other components for particular applications. The method requires applying a small volume of blood, which typically has not been subject to prior treatment (other than optional treatment with an anticoagulant), to the matrix. Timing of the measurement is activated by the apparatus automatically detecting a change in reflectance of the matrix when fluid penetrates the matrix. The change in reflectance over a predetermined time period as a result of formation of reaction product is then related to the amount of analyte in a sample.

The first component of the present invention to be considered is a reagent element, conveniently in the shape of a pad, comprising an inert porous matrix and the component or components of a signal-producing system, which system is capable of reacting with an analyte to produce a light-absorbing reaction product, impregnated into the pores of the porous matrix. The signal-producing system does not significantly impede the flow of liquid through the matrix.

In order to assist in the reading reflectance, it is preferred that the matrix have at least one side which is substantially smooth and flat. Typically, the matrix will be formed into a thin sheet with at least one smooth, flat side. In use, the liquid sample being analyzed is applied to one side of the sheet whereby any assay compound present passes through the reagent element by means of capillary, wicking, gravity flow and/or diffusion actions. The components of the signal producing system present in the matrix will react to give a light absorbing reaction product. Incident light impinges upon the reagent element at a location other than the location to which the sample is applied. Light is reflected from the surface of the element as diffuse reflected light. This diffuse light is collected and measured, for example by the detector of a reflectance spectrophotometer. The amount of reflected light will be related to the amount of analyte in the sample, usually being an inverse function of the amount of analyte in the sample.

THE MATRIX

Each of the components necessary for producing the reagent element will be described in turn. The first component is the matrix itself.

The matrix will be a hydrophilic porous matrix to which reagents may be covalently or non-covalently bound. The matrix will allow for the flow of an aqueous medium through the matrix. It will also allow for binding of protein compositions to the matrix without significantly adversely affecting the biological activity of the protein, e.g. enzymatic activity of an enzyme. To the extent that proteins are to be covalently bound, the matrix will have active sites for covalent bonding or may be activated by means known to the art. The composition of the matrix will be reflective and will be of sufficient thickness to permit the formation of a light-absorbing dye in the void volume or on the surface to substantially affect the reflectance from the matrix. The matrix may be of a uniform composition or a coating on a substrate providing the necessary structure and physical properties.

The matrix will usually not deform on wetting, thus retaining its original conformation and size. The matrix will have a defined absorbtivity, so that the volume which is absorbed can be calibrated within reasonable limits, variations usually being maintained below about 50%, preferably not greater than 10%. The matrix will have sufficient wet strength to allow for routine manufacture. The matrix will permit non-covalently bound reagents to be relatively uniformly distributed on the surface of the matrix.

As exemplary of matrix surfaces are polyamides, particularly with samples involving whole blood. The polyamides are conveniently condensation polymers of monomers of from 4 to 8 carbon atoms, where the monomers are lactams or combinations of diamines and di-carboxylic acids. Other polymeric compositions having comparable properties may also find use. The polyamide compositions may be modified to introduce other functional groups which provide for charged structures, so that the surfaces of the matrix may be neutral, positive or negative, as well as neutral, basic or acidic. Preferred surfaces are positively charged.

When used with whole blood, the porous matrix preferably has pores with an average diameter in the range of from about 0.1 to 2.0 $\mu$m, more preferably from about 0.6 to 1.0 $\mu$m.

A preferred manner of preparing the porous material is to cast the hydrophilic polymer onto a core of nonwoven fibers. The core fibers can be any fibrous material that produce the described integrity and strength, such as polyesters and polyamides. The reagent that will form the light-absorbing reaction product, which is discussed later in detail, is present within the pores of the matrix but does not block the matrix so that the liquid portion of the assay medium, e.g. blood, being analyzed can flow through the pores of the matrix, while particles, such as erythrocytes, are held at the surface.

The matrix is substantially reflective so that it gives a diffuse reflectance without the use of a reflective backing. Preferably at least 25%, more preferably at least 50%, of the incident light applied to the matrix is reflected and emitted as diffuse reflectance. A matrix of less than about 0.5 mm thickness is usually employed, with from about 0.01 to 0.3 mm being preferred. A thickness of from 0.1 to 0.2 mm is most preferred, particularly for a nylon matrix.

Typically, the matrix will be attached to a holder in order to give it physical form and rigidity, although this may not be necessary. FIG. 1 shows one embodiment of the invention in which a thin hydrophilic matrix pad 11 is positioned at one end of a plastic holder 12 by means of an adhesive 13 which directly and firmly attaches the reagent pad to the handle. A hole 14 is present in the plastic holder 12 in the area to which reagent pad 11 is attached so that sample can be applied to one side of the reagent pad and light reflected from the other side.

A liquid sample to be tested is applied to pad 11. Generally, with blood being exemplary of a sample being tested, the reagent pad will be on the order of about 10 mm$^2$ to 100 mm$^2$ in surface area, especially 10 mm$^2$ to 50 mm$^2$ in area, which is normally a volume that 5–10 microliters of sample will more than saturate.

Diffuse reflectance measurements in the prior art have typically been taken using a reflective backing attached to or placed behind the matrix. No such backing is needed or will normally be present during the practice of the present invention, either as part of the reagent element or the reflectance apparatus.

As can be seen from FIG. 1, the support holds reagent pad 11 so that a sample can be applied to one side of the reagent pad while light reflectance is measured from the side of the reagent pad opposite the location where sample is applied.

Figure 2:
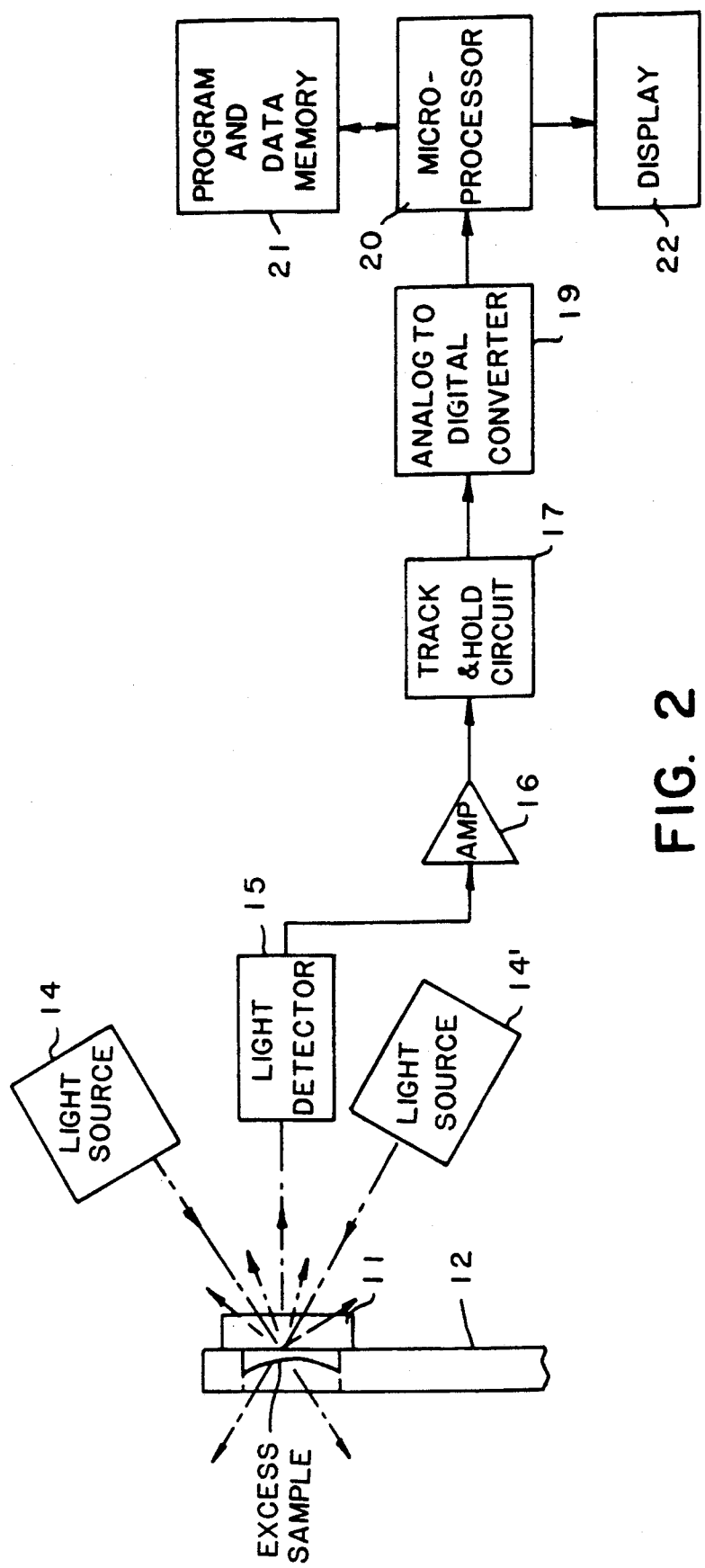
FIG. 2 is a block diagram schematic of an apparatus that can be employed in the practice of the invention.
Figure 3:
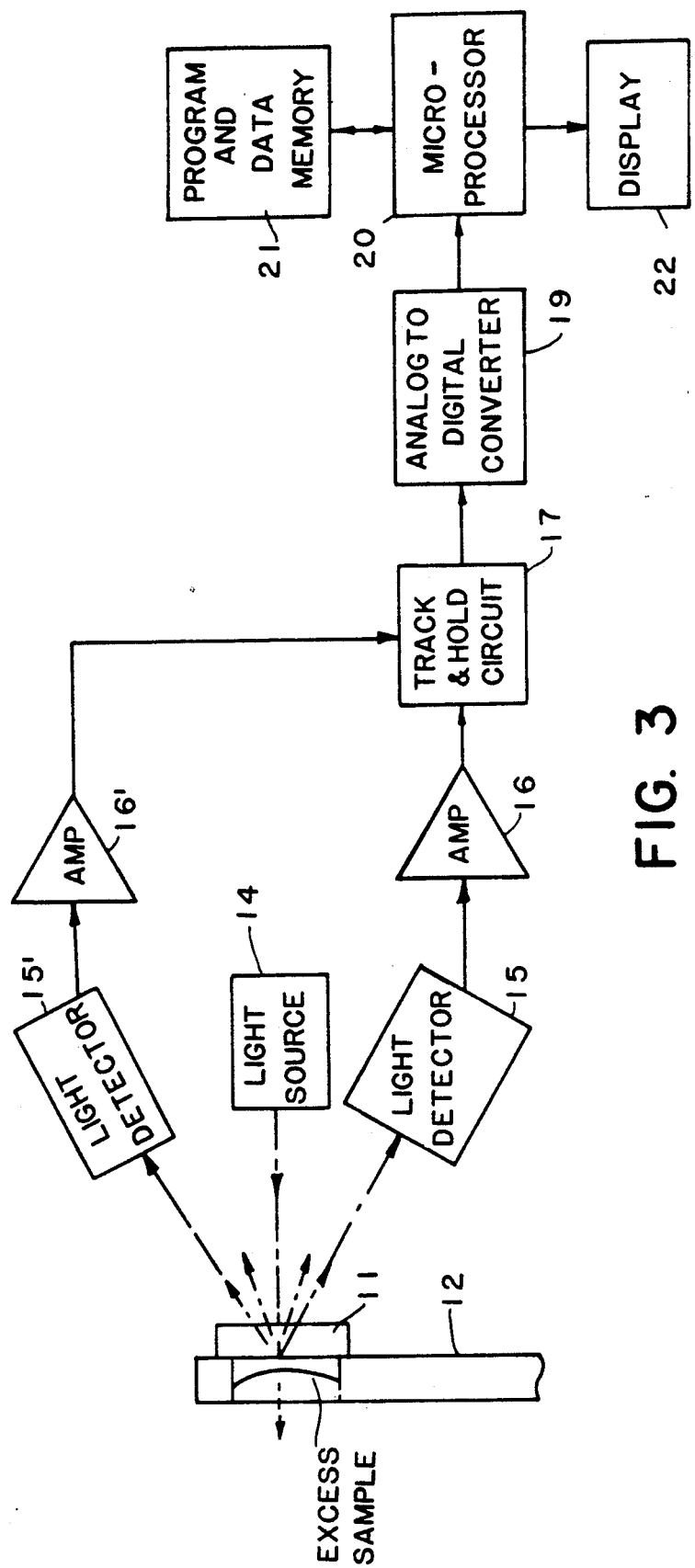
FIG. 3 is a block diagram schematic of an alternate apparatus that can be employed in the practice of the invention.

FIG. 2 shows a system in which the reagent is applied to the side with the hole in the backing handle while light is reflected and measured on the other side of the reagent pad. Other structures than the one depicted may be employed. The pad may take various shapes and forms, subject to the limitations provided herein. The pad will be accessible on at least one surface and usually two surfaces.

The hydrophilic layer (reagent element) may be attached to the support by any convenient means, e.g., a holder, clamp or adhesives; however, in the preferred method it is bonded to the backing. The bonding can be done with any non-reactive adhesive, by a thermal method in which the backing surface is melted enough to entrap some of the material used for the hydrophilic layer, or by microwave or ultrasonic bonding methods which likewise fuse the hydrophilic sample pads to the backing. It is important that the bonding be such as to not itself interfere substantially with the diffuse reflectance measurements or the reaction being measured, although this is unlikely to occur as no adhesive need be present at the location where the reading is taken. For example, an adhesive 13 can be applied to the backing strip 12 followed first by punching hole 14 into the combined strip and adhesive and then applying reagent pad 11 to the adhesive in the vicinity of hole 14 so that the peripheral portion of the reagent pad attaches to the backing strip.

THE CHEMICAL REAGENTS

Any signal producing system may be employed that is capable of reacting with the analyte in the sample to produce (either directly or indirectly) a compound that is characteristically absorptive at a wavelength other than a wavelength at which the assay medium substantially absorbs.

Polyamide matrices are particularly useful for carrying out reactions in which a substrate (analyte) reacts with an oxygen-utilizing oxidase enzyme in such a manner that a product is produced that further reacts with a dye intermediate to either directly or indirectly form a dye which absorbs in a predetermined wavelength range. For example, an oxidase enzyme can oxidize a substrate and produce hydrogen peroxide as a reaction product. The hydrogen peroxide can then react with a dye intermediate or precursor, in a catalysed or uncatalysed reaction, to produce an oxidized form of the intermediate or precursor. This oxidized material may produce the colored product or react with a second precursor to form the final dye.

Nonlimiting examples of analyses and typical reagents include the following materials shown in the following list.

| Analyte and Sample Type | Reagents |
| --- | --- |
| Glucose in blood, serum, urine or other biological fluids, wine, fruit juices or other colored aqueous fluids. Whole blood is a particularly preferred sample type. | Glucose Oxidase, Peroxidase and an Oxygen Acceptor |
| | Oxygen Acceptors include: |
| | 0-dianisidine (1) |
| | 0-toluidine |
| | 0-tolidine (1) |
| | Benzidine (1) |
| | 2,2'-Azinodi-(3-ethylbenzthiazoline sulphonic acid-(6)) (1) |
| | 3-Methyl-2-benzothiazolinone hydrazone plus N,N-dimethylaniline (1) |
| | Phenol plus 4-aminophenazone (1) |
| | Sulfonated 2,4-dichlorophenol plus 4-aminophenazone (2) |
| | 3-Methyl-2-benzothiazolinone hydazone plus 3-(dimethylamino)benzoic acid (3) |
| | 2-Methoxy-4-allyl phenol (4) |
| | 4-Aminoantipyrine- |

| Analyte and Sample Type | Reagents |
|---|---|
| | dimethylaniline (5) |

(1) As reported Clinical Chemistry, Richterich and Columbo, p. 367 and references cited therein.
(2) Analyst, 97, (1972) 142–5.
(3) Anal. Biochem., 105, (1980) 389–397.
(4) Anal. Biochem., 79, (1977) 597–601.
(5) Clinica Chemica Acta, 75, (1977) 387–391 all incorporated herein by reference.

THE ANALYSIS METHOD

The analysis method of this invention relies on a change in absorbance, as measured by diffuse reflectance, which is dependent upon the amount of analyte present in a sample being tested. This change may be determined by measuring the change in the absorbance of the test sample between two or more points in time.

The first step of the assay to be considered will be application of the sample to the matrix. In practice, an analysis could be carried out as follows: First a sample of aqueous fluid containing an analyte is obtained. Blood may be obtained by a finger stick, for example. An excess over matrix saturation in the area where reflectance will be measured (i.e., about 5–10 microliters) of this fluid is applied to the reagent element or elements of the test device. Simultaneous starting of a timer is not required (as is commonly required in the prior art), as will become clear below. Excess fluid can be removed, such as by light blotting, but such removal is also not required. The test device is typically mounted in an instrument for reading light absorbance; e.g., color intensity, by reflectance, prior to application of the sample. Absorbance is measured at certain points in time after application of the sample. Absorbance refers in this application not only to light within the visual wavelength range but also outside the visual wavelength range, such as infrared and ultraviolet radiation. From these measurements of absorbance a rate of color development can be calibrated in terms of analyte level.

THE MEASURING INSTRUMENT

A suitable instrument, such as a diffuse reflectance spectrophotometer with appropriate software, can be made to automatically read reflectance at certain points in time, calculate rate of reflectance change, and, using calibration factors, output the level of analyte in the aqueous fluid. Such a device is schematically shown in FIG. 2 wherein a test device of the invention comprising backing 12 to which reagent pad 11 is affixed is shown. Light source 14, 14' for example a high intensity light emitting diode (LED), projects a beam of light onto the reagent pad. A substantial portion (at least 25%, preferably at least 35%, and more preferably at least 50%, in the absence of reaction product) of this light is diffusively reflected from the reagent pad and is detected by light detector 15, for example a phototransistor that produces an output current proportional to the light it receives. Light source 14, 14' and/or detector 15 can be adapted to generate or respond to a particular wavelength light, if desired. The output of detector 15 is passed to amplifier 16, for example, a linear integrated circuit which converts the phototransistor current to a voltage. The output of amplifier 16 can be fed to track and hold circuit 17. This is a combination linear/digital integrated circuit which tracks or follows the analog voltage from amplifier 16 and, upon command from microprocessor 20, locks or holds the voltage at its level at that time. Analog-to-digital converter 19 takes the analog voltage from track and hold circuit 17 and converts it to, for example, a twelve-bit binary digital number upon command of microprocessor 20. Microprocessor 20 can be a digital integrated circuit. It serves the following control functions: 1) timing for the entire system; 2) reading of the output of analog/digital converter 19; 3) together with program and data memory 21, storing data corresponding to the reflectance measured at specified time intervals; 4) calculating analyte levels from the stored reflectances; and 5) outputing analyte concentration data to display 22. Memory 21 can be a digital integrated circuit which stores data and the microprocessor operating program. Reporting device 22 can take various hard copy and soft copy forms. Usually it is a visual display, such as a liquid crystal or LED display, but it can also be a tape printer, audible signal, or the like. The instrument also can include a start-stop switch and can provide an audible or visible time output to indicate times for applying samples, taking readings, etc., if desired.

REFLECTANCE SWITCHING

In the present invention, the reflectance circuit itself can be used to initiate timing by measuring a drop in reflectance that occurs when the aqueous portion of the suspension solution applied to the reagent pad (e.g., blood) migrates to the surface at which reflectance is being measured. Typically, the measuring device is turned on in a "ready" mode in which reflectance readings are automatically made at closely spaced intervals (typically about 0.2 seconds) from the typically off-white, substantially dry, unreacted reagent strip. The initial measurement is typically made prior to penetration of the matrix by fluid being analyzed but can be made after the fluid has been applied to a location on the reagent element other than where reflectance is being measured. The reflectance value is evaluated by the microprocessor, typically by storing successive values in memory and then comparing each value with the initial unreacted value. When the aqueous solution penetrates the reagent matrix, the drop in reflectance signals the start of the measuring time interval. Drops in reflectance of 5–50% can be used to initiate timing, typically a drop of about 10%. In this simple way there is exact synchronization of assay medium reaching the surface from which measurements are taken and initiation of the sequence of readings, with no requirement of activity by the user.

Although the total systems described in this application are particularly directed to the use of polyamide matrices and particularly to the use of such matrices in determining the concentration of various sugars, such as glucose, and other materials of biological origin, there is no need to limit the reflectance switching aspect of the invention to such matrices. For example, the matrix used with reflectance switching may be formed from any water-insoluble hydrophilic material and any other type of reflectance assay.

PARTICULAR APPLICATION TO GLUCOSE ASSAY

A particular example with regard to detecting glucose in the presence of red blood cells will now be given in order that greater detail and particular advantage can be pointed out. Although this represents a preferred embodiment of the present invention, the invention is not limited to the detection of glucose in blood.

The use of polyamide surfaces to form the reagent element provides a number of desirable characteristics in the present invention. These are that the reagent element is hydrophilic (i.e., takes up reagent and sample readily), does not deform on wetting (so as to provide a flat surface for reflectance reading), is compatible with enzymes (in order to impart good shelf stability), takes up a limited sample volume per unit volume of membrane (necessary in order to demonstrate an extended dynamic range of measurements), and shows sufficient wet strength to allow for routine manufacture.

In a typical configuration, the method is carried out using an apparatus consisting of a plastic holder and the reagent element (the matrix having the signal producing system impregnated therein). The preferred matrix for use in preparing the reagent element is a nylon microfiltration membrane, particularly membranes made from nylon-66 cast on a core of non-woven polyester fibers. Numerous nylon microfiltration membranes of this class are produced commercially by the Pall Ultrafine Filtration Corporation having average pore sizes from 0.1 to 3.0 microns. These materials show mechanical strength and flexibility, dimensional stability upon exposure to water, and rapid wetting.

Many variations in specific chemical structure of the nylon are possible. These include unfunctionalized nylon-66 with charged end groups (sold under the trademark ULTIPORE by Pall Ultrafine Filtration Corporation; "Pall"). Positive charges predominate below pH 6 while negative charges predominate above pH 6. In other membranes the nylon is functionalized before the membrane is formed to give membranes with different properties. Nylons functionalized with carboxy groups are negatively charged over a wide pH range (sold as CARBOXYDYNE by Pall). Nylons can also be functionalized with a high density of positively charged groups on its surface, typically quaternary amine groups, so that they display little variation in charge over a wide pH range (sold as Posidyne by Pall). Such materials are particularly well suited for the practice of the present invention. It is also possible to use membranes having reactive functional groups designed for covalent immobilization of proteins (sold as Biodyne Immuno Affinity membranes by Pall). Such materials can be used to covalently attach proteins, e.g. enzymes, used as reagents. Although all of these materials are usable, nylon having a high density of positively charged groups on its surface provide the best stability of reagents when formulated into a dry reagent pad. Unfunctionalized nylon gives the next best stability with the carboxylated nylons next best.

Desirable results can be obtained with pore sizes ranging from about 0.2–2.0 μm, preferably about 0.5–1.2 μm, and most preferably about 0.8 μm, when used with whole blood.

The form of the handle on which the reagent element is assembled is relatively unimportant as long as the handle allows access to one side of the reagent element by sample and to the other side of the reagent element by incident light whose reflectance is being measured. The handle also aids in inserting the reagent element into the absorbance measuring device so that it registers with the optical system. One example of a suitable handle is a mylar or other plastic strip to which a transfer adhesive such as 3M 465 or Y9460 transfer adhesive has been applied. A hole is punched into the plastic through the transfer adhesive. A reagent element, typically in the form of a thin pad, either containing reagents or to which reagents will later be added, is then applied to the handle by means of the transfer adhesive so that it is firmly attached to the handle in the area surrounding the hole that has been punched through the handle and the transfer adhesive. Such a device is illustrated in FIG. 1, which shows reagent pad 11 attached to a Mylar handle 12 by means of adhesive 13. Hole 14 allows access of the sample or incident light to one side of reagent pad 11 while access to the other side of the reagent pad is unrestricted. All dimensions of the reagent pad and handle can be selected so that the reagent pad fits securely into a reflectance-reading instrument in proximal location to a light source and a reflected-light detector.

If a nylon matrix is selected to form the reagent pad, when the indicated thicknesses are employed, it is preferred to have the reagent pad supported by the holder in such a manner that no more than 6 mm, measured in any direction, is unsupported by the holder at the location were the sample is applied and light reflectance is measured. Larger unsupported areas tend to provide inadequate dimensional stability to the membrane so that measurement of reflectance from the surface is adversely affected. A 5 mm diameter hole 14 in the reagent strip shown in FIG. 1 works quite satisfactorily.

There is no particular limit on the minimum diameter of such a hole, although diameters of at least 2 mm are preferred for ease of manufacture, sample application, and light reflectance reading.

Although a number of dyes could be used as indicators, the choice will depend upon the nature of the sample. It is necessary to select a dye having an absorbance at a wavelength different from the wavelength at which red blood cells absorb light, with whole blood as the assay medium, or other contaminants in the solution being analyzed with other assay media. The MBTH-DMAB dye couple (3-methyl-2-benzothiazolinone hydrazone hydrochloride and 3-dimethylaminobenzoic acid), although being previously described as suitable for color development for peroxidase labels in enzyme immunoassays, has never been used in a commercial glucose measuring reagent. This dye couple gives greater dynamic range and shows improved enzymatic stability as compared to traditional dyes used for glucose measurement, such as benzidine derivatives. Furthermore, the MBTH-DMAB dye couple is not carcinogenic, a characteristic of most benzidine derivatives.

Another dye couple that can be used in the measurement of glucose is the AAP-CTA (4-aminoantipyrene and chromotropic acid) couple. Although this couple does not provide as broad a dynamic range as MBTH-DMAB, it is stable and suitable for use in the practice of the present invention when measuring glucose. Again, the AAP-CTA dye couple provides an expanded dynamic range and greater enzymatic activity stability than the more widely used benzidine dyes.

The use of the MBTH-DMAB couple allows for correction of hematocrit and degree of oxygenation of blood with a single correction factor. The more typically used benzidine dyes do not permit such a correction. The dye forms a chromophore that absorbs at approximately 635 nm but not to any significant extent at 700 nm. Slight variations in measuring wavelengths (± about 10 nm) are permitted. At 700 nm both hematocrit and degree of oxygenation can be measured by measuring blood color. Furthermore, light emitting diodes (LED) are commercially available for both 635 nm and 700 nm measurements, thereby simplifying mass-production of a device. By using the preferred membrane pore size described above and the subject reagent formulation both hematocrit and oxygenation behavior can be corrected by measuring at the single 700 nm wavelength.

Two additional conditions were found to provide particular stability and long shelf life for a glucose oxidase/peroxidase formulation on a polyamide matrix. These use a pH in the range of 3.8 to 5.0, preferably about 3.8 to 4.3, most preferably about 4.0, and use of a concentrated buffer system for applying the reagents to the matrix. The most effective buffer was found to be 10 weight percent citrate buffer, with concentrations of from 5-15% being effective. These are weight/volume percentages of the solution in which the reagents are applied to the matrix. Other buffers can be used on the same molar basis. Greatest stability was achieved using a low pH, preferably about pH 4, an MBTH-DMAB dye system, and a high enzyme concentration of approximately 500-1000 U/ml of application solution.

In preparing the MBTH-DMAB reagent and the enzyme system that forms the remainder of the signal producing system, it is not necessary to maintain exact volumes and ratios although the suggested values below give good results. Reagents are readily absorbed by the matrix pad when the glucose oxidase is present in a solution at about 27-54% by volume, the peroxidase is present at a concentration of about 2.7-5.4 mg/ml, MBTH is present at a concentration of about 4-8 mg/ml, and DMAB is present at a concentration of about 8-16 mg/ml. The DMAB-MBTH weight ratio is preferably maintained in the range of (1-4):1, preferably about (1.5-2.5):1, most preferably about 2:1.

The basic manufacturing techniques for the reagent element are, once established, straightforward. The membrane itself is strong and stable, particularly when a nylon membrane of the preferred embodiment is selected. Only two solutions are necessary for applying reagent, and these solutions are both readily formulated and stable. The first generally contains the dye components and the second generally contains the enzymes. When using the MBTH-DMAB dye couple, for example, the individual dyes are dissolved in an aqueous organic solvent, typically a 1:1 mixture of acetonitrile and water. The matrix is dipped into the solution, excess liquid is removed by blotting, and the matrix is then dried, typically at 50°-60° C. for 10-20 minutes. The matrix containing the dyes is then dipped into an aqueous solution containing the enzymes. A typical formulation would contain the peroxidase and glucose oxidase enzymes as well as any desired buffer, preservative, stabilizer, or the like. The matrix is then blotted to remove excess liquid and dried as before. A typical formulation for the glucose reagent is as follows:

DYE DIP

Combine:
40 mg MBTH,
80 mg DMAB,
5 ml acetonitrile, and
5 ml water.
Stir until all solids are dissolved and pour onto a glass plate or other flat surface. Dip a piece of POSIDYNE membrane (Pall Co.), blot off excess liquid, and dry at 56° C. for 15 minutes.

ENZYME DIP

Combine:
6 ml water,
10 mg EDTA, disodium salt,
200 mg Poly Pep, low viscosity, (Sigma)
0.668 g sodium citrate,
0.523 g citric acid,
2.0 ml 6 wt % Gantrez AN-139 dissolved in water (GAF)
30 mg horseradish peroxidase, 100 units/mg, and
3.0 ml glucose oxidase, 2000 units/ml.
Stir until all solids are dissolved and pour onto a glass plate or other flat surface. Dip a piece of membrane previously impregnated with dyes, blot off excess liquid, and dry at 56° C. for 15 minutes.

The electronic apparatus used to make the reflectance readings minimally contains a light source, a reflected light detector, an amplifier, an analog to digital converter, a microprocessor with memory and program, and a display device.

The light source typically consists of a light emitting diode (LED). Although it is possible to use a polychromic light source and a light detector capable of measuring at two different wavelengths, a preferred apparatus would contain two LED sources or a single diode capable of emitting two distinct wavelengths of light. Commercially available LEDs producing the wavelengths of light described as being preferred in the present specification include a Hewlett Packard HLMP-1340 with an emission maximum at 635 nm and a Hewlett Packard QEMT-1045 with a narrow-band emission maximum at 700 nm. Suitable commercially available light detectors include a Hammamatsu 5874-18K and a Litronix BPX-65.

Although other methods of taking measurements are feasible, the following method has provided the desired results. Readings are taken by the photo-detector at specified intervals after timing is initiated. The 635 nm LED is powered only during a brief measuring time span that begins approximately 20 seconds after the start time as indicated by reflectance switching. If this reading indicates that a high level of glucose is present in the sample, a 30-second reading is taken and used in the final calculation in order to improve accuracy. Typically, high levels are considered to begin at about 250 mg/dl. The background is corrected with a 700 nm reading taken about 15 seconds after the start of the measurement period. The reading from the photodetector is integrated over the interval while the appropriate LED is activated, which is typically less than one second. The raw reflectance readings are then used for calculations performed by the microprocessor after the signal has been amplified and converted to a digital signal. Numerous microprocessors can be used to carry out the calculation. An AIM65 single-board microcomputer manufactured by Rockwell International has proven to be satisfactory.

The present methods and apparatuses allow a very simple procedure with minimum operational steps on the part of the user. In use, the reagent strip is placed in the detector so that the hole in the strip registers with the optics of the detecting system. A removable cap or other cover is placed over the optics and strip to shield the assembly from ambient light. The measurement sequence is then initiated by pressing a button on the measuring apparatus that activates the microcomputer to take a measurement of reflected light from the unreacted reagent pad, called an $R_{dry}$ reading. The cap is then removed and a drop of blood is applied to the reagent pad, typically while the reagent pad is registered with the optics and the reading device. It is preferred that the reagent strip be left in register with the optics in order to minimize handling. The instrument is capable of sensing the application of blood or other sample by a decrease in the reflectance when the sample passes through the matrix and reflected light is measured on the opposite side. The decrease in reflectance initiates a timing sequence which is described in detail at other locations in this specification. The cover should be replaced within 15 seconds of sample application, although this time may vary depending on the type of sample being measured. Results are typically displayed at approximately 30 seconds after blood application when a blood glucose sample is being measured, although a 20 second reaction is permissible for glucose samples having a concentration of glucose of less than 250 mg/dl. If other samples are being measured, suitable times for displaying the result may differ and can be readily determined from the characteristics of the reagent/sample selected.

A particularly accurate evaluation of glucose level (or any other analyte being measured) can be made using the background current, i.e., the current from the photodetector with power on but with no light reflected from the reagent pad, in order to make a background correction. It has been demonstrated that over a 2-3 month period that this value does not change for a particular instrument prepared according to the preferred embodiments of this specification, and it is possible to program this background reading into the computer memory as a constant. With a slight modification of the procedure, however, this value can be measured with each analysis for more accurate results. In the modified procedure the meter would be turned on with the lid closed before the reagent strip is in place, and the background current would be measured. The test strip would then be inserted into the meter with the cover closed, an $R_{dry}$ measurement taken, and the procedure continued as described above. With this modified procedure the background current does not need to be stable throughout the life of the meter, thereby providing more accurate results.

The raw data necessary for calculating a result in a glucose assay are a background current reported as background reflectance, $R_b$, as described above; a reading of the unreacted test strip, $R_{dry}$, also described above; and an endpoint measurement. Using the preferred embodiments described herein, the endpoint is not particularly stable and must be precisely timed from the initial application of blood. However, the meter as described herein performs this timing automatically. For glucose concentrations below 250 mg/dl, a suitably stable endpoint is reached in 20 seconds, and a final reflectance, $R_{20}$, is taken. For glucose concentrations up to 450 mg/dl, a 30-second reflectance reading, $R_{30}$, is adequate. Although the system described herein displays good differentiation up to 800 mg/dl of glucose, the measurement is somewhat noisy and inaccurate above 450 mg/dl, although not so great as to cause a significant problem. Longer reaction times should provide more suitable readings for the higher levels of glucose concentration.

The 700 nm reflectance reading for the dual wavelength measurement is typically taken at 15 seconds ($R_{15}$). By this time blood will have completely saturated the reagent pad. Beyond 15 seconds the dye reaction continues to take place and is sensed, to a small part, by a 700 nm reading. Accordingly, since dye absorption by the 700 nm signal is a disadvantage, readings beyond 15 seconds are ignored in the calculations.

The raw data described above are used to calculate parameters proportional to glucose concentration which can be more easily visualized than reflectance measurements. A logarithmic transformation of reflectance analogous to the relationship between absorbance and analyte concentration observed in transmission spectroscopy (Beer's Law) can be used if desired. A simplification of the Kubelka-Monk equations, derived specifically for reflectance spectroscopy, have proven particularly useful. In this derivation K/S is related to analyte concentration with K/S defined by Equation 1.

$$K/S-t=(1-R^*t)^2/(2\times R^*t) \qquad (1)$$

$R^*t$ is the reflectivity taken at a particular endpoint time, t, and is the absorbed fraction of the incident light beam described by Equation 2, where $R_t$ is the endpoint reflectance, $R_{20}$ or $R_{30}$.

$$R^*t=(R_t-R_b)/(R_{dry}-R_b) \qquad (2)$$

$R^*t$ varies from 0 for no reflected light ($R_b$) to 1 for total reflected light ($R_{dry}$). The use of reflectivity in the calculations greatly simplifies meter design as a highly stable source and a detection circuit become unnecessary since these components are monitored with each $R_{dry}$ and $R_b$ measurement.

For a single wavelength reading K/S can be calculated at 20 seconds (K/S−20) or 30 seconds (K/S−30). The calibration curves relating these parameters to YSI (Yellow Springs Instruments) glucose measurements can be precisely described by the third order polynomial equation outlined in Equation 3.

$$YSI=a_0+a_1(K/S)+a_2(K/S)^2+a_3(K/S)^3 \qquad (3)$$

The coefficients for these polynomials are listed in Table 1.

TABLE 1

| Coefficients for Third Order Polynomial Fit of Single Wavelength Calibration Curves | | |
|---|---|---|
| | K/S-20 | K/S-30 |
| $a_0$ | −55.75 | −55.25 |
| $a_1$ | 0.1632 | 0.1334 |
| $a_2$ | $-5.765 \times 10^{-5}$ | $-2.241 \times 10^{-5}$ |
| $a_3$ | $2.58 \times 10^{-8}$ | $1.20 \times 10^{-8}$ |

The single chemical species being measured in the preferred embodiments is the MBTH-DMAB indamine dye and the complex matrix being analyzed is whole blood distributed on a 0.8 μm Posidyne membrane. A review entitled "Application of Near Infra Red Spectrophotometry to the Nondestructive Analysis of Foods: A Review of Experimental Results", *CRC Critical Reviews in Food Science and Nutrition*, 18(3) 203-30 (1983), describes the use of instruments based on the measurement of an optical density difference $\Delta OD$ ($\lambda_a-\lambda_b$) where $OD\lambda_a$ is the optical density of the wavelength corresponding to the absorption maximum of a component to be determined and $OD\lambda_b$ is the optical density at a wavelength where the same component does not absorb significantly.

The algorithm for dual wavelength measurement is by necessity more complex than for single wavelength measurement but is much more powerful. The first order correction applied by the 700 nm reading is a simple subtraction of background color due to blood. In order to make this correction, a relationship between absorbance at 635 nm and 700 nm due to blood color can be and was determined by measuring blood samples with 0 mg/dl glucose over a wide range of blood color. The color range was constructed by varying hematocrit, and fairly linear relationships were observed. From these lines the $K/S-15$ at 700 nm was normalized to give equivalence to the $K/S-30$ at 635 nm. This relationship is reported in Equation 4, where $K/S-15\ n$ is the normalized $K/S-15$ at 700 nm.

$$K/S-15\ n = (K/S-15 \times 1.54) - 0.133 \quad (4)$$

Note that the equivalence of the normalized 700 nm signal and the 635 nm signal is only true at zero glucose. The expressions from which the calibration curves were derived are defined by Equations 5 and 6.

$$K/S-20/15 = (K/S-20) - (K/S-15\ n) \quad (5)$$

$$K/S-30/15 = (K/S-30) - (K/S-15\ n) \quad (6)$$

These curves are best fit by fourth-order polynomial equations similar to Equation 3 to which a fourth-order term in K/S is added. The computer-fit coefficients for these equations are listed in Table 2.

TABLE 2

Coefficients for Fourth-Order Polynomial Fit of Dual Wavelength Calibration Curves

| | K/S-20/15 | K/S-30/15 |
|---|---|---|
| $a_0$ | −0.1388 | 1.099 |
| $a_1$ | 0.1064 | 0.05235 |
| $a_2$ | $6.259 \times 10^{-5}$ | $1.229 \times 10^{-4}$ |
| $a_3$ | $-6.12 \times 10^{-8}$ | $-5.83 \times 10^{-8}$ |
| $a_4$ | $3.21 \times 10^{-11}$ | $1.30 \times 10^{-11}$ |

A second order correction to eliminate errors due to chromatography effects has also been developed. Low hematocrit samples have charcteristically low 700 nm readings compared to higher hematocrit samples with the same 635 nm reading. When the ratio of $(K/S-30)/(K/S-15)$ is plotted versus $K/S-30$ over a wide range of hematocrits and glucose concentrations, the resulting line on the graph indicates the border between samples which display chromatography effects (above the curve) and those that do not (below the curve). The $K/S-30$ for the samples above the curve are corrected by elevating the reading to correspond to a point on the curve with the same $(K/S-30)/(K/S-15)$.

The correction factors reported above were tailor made to fit a single instrument and a limited number of reagent preparations. The algorithm can be optimized for an individual instrument and reagent in the same manner that is described above.

In summary, the system of the present invention minimizes operator actions and provides numerous advantages over prior art reflectance-reading methods. When compared to prior methods for determining glucose in blood, for example, there are several apparent advantages. First, the amount of sample required to saturate the thin reagent pad is small (typically 5-10 microliters). Second, operator time required is only that necessary to apply the sample to the thin hydrophilic layer and close the cover (typically 4-7 seconds). Third, no simultaneous timing start is required. Fourth, whole blood can be used. The method does not require any separation or utilization of red-cell-free samples and likewise can be used with other deeply colored samples.

Several unobvious advantages arise as a result of the practice of the present invention with whole blood. Normally, aqueous solutions (like blood) will penetrate a hydrophilic membrane to give a liquid layer on the opposite side of the membrane, a surface that is then not suited for a reflectance measurement. It has been discovered, however, that blood, apparently because of interactions of red blood cells and proteins in the blood with the matrix, will wet the polyamide matrix without having an excess liquid penetrate the porous matrix to interfere with the reflectance reading on the opposite side of the matrix.

Furthermore, the thin membranes used in the present invention would be expected when wet to transmit light and return only a weak signal to the reflectance measuring device. Prior teachings have generally indicated that a reflective layer is necessary behind the matrix in order to reflect sufficient light. In other cases a white pad has been placed behind the reagent pad prior to color measurement. In the present case, neither a reflective layer or a white pad is required. In fact, the invention is typically carried out with a light-absorbing surface behind the reagent element when incident light is impinged upon the matrix. Using a light-absorbing surface behind the reagent element, coupled with measuring reflectance at two different wavelengths, allows acceptable reflectance measurements to be obtained without removal of excess liquid from the matrix, thereby eliminating a step typically required by previous teachings.

The invention now being generally described, the same will be better understood by reference to the following specific examples which are presented for purposes of illustration only and are not to be considered limiting of the invention unless so specified.

EXAMPLE I

In this and the following examples, "MPX" refers to the system of the present invention.

REPRODUCIBILITY

One male blood sample (JG, hematocrit=45) was used to collect the reproducibility data set forth in Tables 3-5.

TABLE 3

Reproducibility of a Single Wavelength MPX System

| YSI (mg/dl) | Average (mg/dl) | | S.D. (mg/dl) | | % C.V. | |
|---|---|---|---|---|---|---|
| | 20 sec. | 30 sec. | 20 sec. | 30 sec. | 20 sec. | 30 sec. |
| 25 | 23.1 | 23.0 | 2.1 | 2.04 | 9.1 | 9.0 |
| 55 | 53.5 | 53.2 | 3.19 | 3.32 | 6.0 | 6.3 |
| 101 | 101 | 101 | 3.0 | 3.3 | 3.0 | 3.3 |
| 326 | 326.6 | 327 | 13.3 | 9.8 | 4.1 | 3.0 |
| 501 | | 503 | | 17.1 | | 3.4 |
| 690 | | 675 | | 28 | | 4.15 |
| 810 | | 813 | | 37 | | 4.5 |

TABLE 4

Reproducibility of a Dual Wavelength MPX System

| YSI (mg/dl) | Average (mg/dl) | | S.D. (mg/dl) | | % C.V. | |
|---|---|---|---|---|---|---|
| | 20 sec. | 30 sec. | 20 sec. | 30 sec. | 20 sec. | 30 sec. |
| 25 | 25 | 27 | 1.34 | 1.55 | 5.4 | 5.7 |

TABLE 4-continued

Reproducibility of a Dual.Wavelength MPX System

| YSI | Average (mg/dl) | | S.D. (mg/dl) | | % C.V. | |
|---|---|---|---|---|---|---|
| (mg/dl) | 20 sec. | 30 sec. | 20 sec. | 30 sec. | 20 sec. | 30 sec. |
| 55 | 55 | 57.4 | 2.58 | 2.62 | 4.7 | 4.6 |
| 101 | 101 | 101.5 | 2.55 | 2.18 | 2.5 | 2.1 |
| 326 | 332 | 330 | 15.0 | 7.1 | 4.5 | 2.1 |
| 501 | | 505 | | 21.3 | | 4.2 |
| 690 | | 687 | | 22.8 | | 3.3 |
| 810 | | 817 | | 30.4 | | 3.7 |

TABLE 5

Reproducibility of a 3.0 mm Diameter Aperture

| | % C.V. | |
|---|---|---|
| YSI (mg/dl) | 4.7 mm | 3.0 mm |
| 55–100 | 4.8 | 4.9 |
| 300 | 3.0 | 5.0 |
| 600 | 3.8 | 5.5 |
| avg. | 3.9 | 5.1 |

The blood was divided into aliquots and spiked with glucose across a range of 25-800 mg/dl. Twenty determinations were made at each glucose test level from strips taken at random from a 500 strip sample (Lot FJ4-49B). The results of this study lead to the following conclusions:

1. Single vs. Dual Wavelength: The average C.V. for the 30-second dual result was 3.7% vs. 4.8% for the 30-second single wavelength result, an improvement of 23% across a glucose range of 25-810 mg/dl. There was a 33% improvement in C.V. in the 25-326 mg/dl glucose range. Here the C.V. decreased from 5.4% to 3.6%, a significant improvement in the most used range. The 20-second dual wavelength measurement gave similar improvements in C.V. compared to the single wavelength measurement in the 25-325 mg/dl range (Tables 3 and 4).

2. Dual Wavelength, 20 vs. 30-second Result: The average C.V. for a 20-second result in the 25-100 mg/dl range is nearly identical to the 30-second reading, 4.2% vs. 4.1%. However, at 326 mg/dl the 30-second reading has a C.V. of 2.1% and the 20-second result a C.V. of 4.5%. As was seen in the K/S−20 response curve, the slope begins to decrease sharply above 250 mg/dl. This lead to poor reproducibility at glucose levels greater than 300 for the 20-second result. From this reproducibility data the cutoff for the 20-second result is somewhere between 100 and 326 mg/dl. A cutoff of 250 mg/dl was later determined from the results of the recovery study set forth in Example II.

3. Aperture Size: A smaller optics aperture size, 3.0 mm vs. 5.0 mm., was investigated. Initial experimentation using a 10-replicate, hand-dipped disk sample did show improved C.V.s with the 3.0 mm aperture, apparently because of easier registration with the system optics. However, when machine-made roll membrane was used, the average C.V. (Table 5) of the larger aperture, 4.7 mm, was 3.9% vs. an average C.V. for the 3.0 mm aperture of 5.1%. This 30% increase in C.V. was probably due to the uneven surface of the roll membrane lot as discussed below.

EXAMPLE II

RECOVERY

For comparison of the present method (MPX) against a typical prior art method using a Yellow Springs Instrument Model 23A glucose analyser manufactured by Yellow Springs Instrument Co., Yellow Springs, Ohio (YSI), blood from 36 donors was tested. The donors were divided equally between males and females and ranged in hematocrit from 35 to 55%. The blood samples were used within 30 hours of collection, with lithium heparin as the anti-coagulant. Each blood sample was divided into aliquots and spiked with glucose to give 152 samples in the range of 0-700 mg/dl glucose. Each samples was tested in duplicate for a total of 304 data points.

Response curves were constructed from these data and glucose values then calculated from the appropriate equation (Tables 1 and 2). These MPX glucose values were then plotted vs. the YSI values to give scattergrams.

Comparison of MPX Systems: For both the 20-second and 30-second measurement times there is visually more scatter in the single-wavelength scattergrams than the dual-wavelength scattergrams. The 20-second reading becomes very scattered above 250 mg/dl but the 30-second measurement does not have wide scatter until the glucose level is ≧500 mg/dl.

These scattergrams were quantitated by determining the deviations from YSI at various glucose ranges. The following results were obtained.

TABLE 6

Accuracy of MPX from Recovery Data

| MPX Wavelength | Measurement Time (sec.) | S.D. (mg/dl) 0–50 | C.V. for Range* | | |
|---|---|---|---|---|---|
| | | | 50–250 | 250–450 | 450–700 |
| Single | 20 | ±5.6 | 7.2 | 14.5 | — |
| Single | 30 | ±6.9 | 7.1 | 8.8 | 10.2 |
| Dual | 20 | ±2.3 | 5.3 | 12.8 | — |
| Dual | 30 | ±2.19 | 5.5 | 5.8 | 8.4 |

Note: These are inter method C.V.s.
a. The dual wavelength system gave C.V.s that ranged 30% lower than the single wavelength system.
b. The single wavelength system, from 0–50 mg/dl, showed a S.D. of ±6–7 mg/dl whereas the S.D. for a dual wavelength measurement was only ±2.2 mg/dl.
c. The cutoff for a 30-second MPX measurement is 250 mg/dl. For the 50–250 mg/dl range both the 20- and 30-second measurements gave similar inter-method C.V.s (approximately 7% for single wavelength, 5.5% for dual wavelength). However, in the 250–450 mg/dl range inter-method C.V.s more than double for the 20-second reading to 14.5% for the single and 12.8% for the dual wavelength.
d. The 30-second reading was unusable above 450 mg/dl for both the single and dual wavelength measurement (C.V.s of 10.2 and 8.4%).

In conclusion, two MPX systems gave optimum quantitation in the 0–450 mg/dl range.

1. MPX 30 Dual: This dual wavelength system gave a 30-second measurement time with a 95% confidence limit (defined as the probability of a measurement being within 2 S.D. of the YSI) of 11.3% (C.V.) for the range from 50-450 mg/dl (Table 7) and ±4.4 mg/dl (S.D.) for 0-50 mg/dl.

2. MPX 30/20 Dual: This dual wavelength system gave a 20-second measurement time in the 0-250 mg/dl range and a 30-second time for the 250-450 range. The 95% confidence limits are nearly identical to the MPX 30 Dual System (Table 7), 11.1% (C.V.) for 50-450 mg/dl and ±4.6 mg/dl (S.D. for 0-50 mg/dl).

TABLE 7

Comparison of 95% Confidence Limits for MPX, GlucoScan Plus and Accu-Chek bG* Reagent Strips

| Measuring Range | MPX Single Wavelength | | MPX Dual Wavelength | |
|---|---|---|---|---|
| mg/dl | 20 sec. | 30 sec. | 20 sec. | 30 sec. |
| 0-50 | 11.2 mg/dl | 13.8 mg/dl | 4.6 mg/dl | 4.4 mg/dl |
| 50-250 | 14.4% | 14.2% | 10.6% | 11.0% |
| 250-450 | — | 17.6% | — | 11.6% |
| 77-405 | GlucoScan Plus (Drexler Clinical) | | | 15.9% |
| 77-405 | Accu-Chek bG (Drexler Clinical) | | | 10.7% |
| 50-450 | MPX 20/30 Dual Hybrid | | | 11.1% |
| 50-450 | MPX 30 Dual | | | 11.3 |

*Confidence limits for MPX were from the YSI. The confidence limits for GlucoScan Plus and Accu-Chek bG were from the regression equation vs. YSI which eliminates bias due to small differences in calibration.

EXAMPLE III

STABILITY

Most of the bench-scale work carried out in optimizing stability was completed using hand-dipped 0.8 μm Posidyne membrane disks. The specific dye/enzyme formulation was set forth previously.

1. Room Temperature (RT) Stability: This study attempted to chart any change in response of the 0.8μ Posidyne membrane reagent stored at 18°-20° C. over silica gel desiccant. After 2.5 months there was no noticeable change as measured by the response of a room temperature sample vs. the response of a sample stored at 5° C. Each scattergram represented a glucose range of 0-450 mg/dl.

2. Stability at 37° C.: A 37° C. stability study using the same reagent as the RT study was carried out. The differences in glucose values of reagent stressed at 37° C. vs. RT reagent, for strips stressed with and without adhesive, was plotted over time. Although the data was noisy, due to the poor reproducibility of handmade strips, the stability was excellent for strips whether they were stressed with or without adhesive.

3. Stability at 56° C.: Eight 5- to 6-day stability studies were carried out using different preparations of a similar formulation on disk membrane (Table 8). For the low glucose test level (80-100 mg/dl) the average gulcose value dropped upon stressing by 3.4%, with the highest drop being 9.55%. At the high test level (280-320 mg/dl) the glucose reading declined by an average of 3.4%, the largest decline being 10.0%.

TABLE 8

Stability of pH = 4.0, 0.8 μm Posidyne Disk Reagent Formulation Stressed for 5 to 6 Days at 56° C.

| | % Difference (56° C. vs. RT Sample) | |
|---|---|---|
| Sample No. | YSI (80-100 mg/dl) | YSI (280-320 mg/dl) |
| FJ22B | −6.25 | +5.4 |
| FJ27A | −4.0 | −5.14 |
| FJ28B | −2.4 | −5.3 |
| FJ30H | −9.55 | −10.0 |
| FJ31C | +4.43 | −1.24 |
| FJ36 | −3.2 | −8.5 |
| FJ48B* | −3.0 | 0.0 |
| GM48A* | −3.0 | −2.5 |
| Average of 8 | −3.4 | −3.4 |

*These two samples contained twice the normal concentration of enzyme and dye.

A study of the 56° C. stressing of this membrane over a 19-day period showed no major difference for strips stressed with or without adhesive. In both cases the 19-day decline in glucose value was <15% at low test levels (80-100) and 300 mg/dl. Another 56° C. study using hand-dipped 0.8 μm Posidyne membrane with twice the normal concentration of enzyme and dye was completed. Two separate preparations of the same formulation were made up and the stability measured over a 14-day period. The average results of the two studies were plotted. Changes were within ±10% over the 14-day period at both the high and low glucose test level. These data show this formulation to be particularly stable.

EXAMPLE IV

SAMPLE SIZE

The sample size requirements for MPX are demonstrated in Table 9.

TABLE 9

Effect of Sample Size on MPX Measurements

| Sample Size (μl) | Dual Wavelength | | | | Average | Single Wavelength | | | | Average |
|---|---|---|---|---|---|---|---|---|---|---|
| | Low Glucose YSI = 56 | | | | | | | | | |
| 3 | 41 | 50 | 39 | 31 | 40 | 31 | 42 | 30 | 19 | 30 |
| 4 | 44 | 49 | 49 | 49 | 48 | 41 | 45 | 44 | 45 | 44 |
| 5 | 54 | 48 | 49 | 51 | 50 | 50 | 49 | 48 | 49 | 49 |
| 10 | 48 | 48 | 50 | 47 | 48 | 54 | 53 | 56 | 55 | 54 |
| 20 | 49 | 49 | 49 | 50 | 49 | 55 | 57 | 58 | 60 | 58 |
| | High Glucose YSI = 360 | | | | | | | | | |
| 3 | 301 | 260 | 276 | 286 | 280 | 274 | 232 | 244 | 260 | 252 |
| 4 | 383 | 378 | 367 | 341 | 367 | 361 | 356 | 342 | 318 | 344 |
| 5 | 398 | 402 | 382 | 370 | 388 | 378 | 387 | 366 | 351 | 370 |
| 10 | 364 | 362 | 378 | 368 | 368 | 356 | 358 | 379 | 369 | 366 |
| 20 | 375 | 370 | 380 | 378 | 376 | 380 | 382 | 389 | 385 | 384 |

The volumes reported in the table were transferred to the reagent pad shown in FIG. 1 using a micro pipet. When blood from a finger stick is applied to a strip the total sample cannot be transferred, therefore the volumes reported here do not represent the total sample size needed to be squeezed from the finger for the analysis. A 3-μl sample is the minimum necessary to completely cover the reagent pad circle. This does not provide enough sample to completely saturate the reagent pad and MPX gives low results. A 4-μl sample barely saturates the reagent pad, while a 5-μl sample is clearly adequate. A 10-μl sample is a large shiny drop and a 20-μl sample is a very large drop and is only likely to be used when blood from a pipet is used for sampling.

At low glucose concentration the single wavelength result has some dependence on sample size which is completely eliminated using the dual wavelength measurement. Although this dependence with the single wavelength might be considered acceptable, it is clearly undesirable.

EXAMPLE V

REPRODUCIBILITY

Experimental measurements described above were always run in replicate, usually 2, 3 or 4 determinations per data point. These sets have always shown close agreement even for samples with extreme hematocrits or extreme oxygen levels. C.V.s were well below 5%. It appears, therefore, that reproducibility is very good to excellent.

The subject invention provides for many advantages over systems which are presently available commercially or have been described in the literature. The protocols are simple and require little technical skill and are relatively free of operator error. The assays can be carried out rapidly and use inexpensive and relatively harmless reagents, important considerations for materials employed in the home. The user obtains results which can be understood and used in conjunction with maintenance therapy. In addition, the reagents have long shelf lives, so that the results obtained will be reliable for long periods of time. The equipment is simple and reliable and substantially automatic.

All patents and other publications specifically identified in this specification are indicative of the level of skill of those of ordinary skill in the art to which this invention pertains and are herein individually incorporated by reference to the same extent as would occur if each reference were specifically and individually incorporated by reference.

The invention now being fully described, it will be apparent to one of ordinary skill in the art that many modifications and changes can be made thereto without departing from the spirit or scope of the invention as defined in the following claims.

What is claimed is:

1. A method of causing an analytical measurement to be made in a reflectance-reading device at the end of a predetermined time period after an analyte reacts with a reagent in a porous, reflectance-reading matrix located in said device, which comprises:

taking a first reflectance reading from a dry first surface of said porous matrix prior to application of a sample of body fluid suspected of containing said analyte to a second surface of said porous matrix from which said sample can travel to said first surface by capillary action and react with said reagent in said porous matrix if said analyte is present in said sample;

applying said sample to said second surface of said porous matrix;

taking an additional reflectance reading from said first surface after said sample is applied to said porous matrix;

comparing said additional reflectance reading to said first reflectance reading;

initiating said predetermined time period upon a predetermined drop in reflectance sufficient to indicate that said sample has reached said first surface; and taking a measurement reflectance reading at the end of said predetermined time period without having determined the time at which said sample was initially applied to said porous matrix.

2. A method according to claim 1, wherein said reagent comprises a dye precursor bound to the matrix.

* * * * *